United States Patent [19]

Donovan

[11] Patent Number: 5,671,634
[45] Date of Patent: Sep. 30, 1997

[54] MEASURING ADHESION OF CYLINDER BORE COATINGS

[75] Inventor: David Alvin Donovan, Chelsea, Mich.

[73] Assignee: Ford Global Technologies, Inc., Dearborn, Mich.

[21] Appl. No.: 703,923

[22] Filed: Aug. 22, 1996

[51] Int. Cl.⁶ ................................................ G01N 19/00
[52] U.S. Cl. ........................................... 73/150 A; 73/827
[58] Field of Search ................................ 73/37, 38, 40, 73/150 A, 827

[56] References Cited

U.S. PATENT DOCUMENTS

| | | | |
|---|---|---|---|
| 2,694,924 | 11/1954 | Matlock et al. | 73/37 |
| 3,952,566 | 4/1976 | Jacobson . | |
| 4,393,699 | 7/1983 | Seiler, Jr. | 73/150 A |
| 4,491,014 | 1/1985 | Seiler, Jr. . | |
| 4,548,083 | 10/1985 | Schuerer et al. . | |
| 4,567,758 | 2/1986 | Fisher et al. . | |
| 4,586,371 | 5/1986 | Ivie et al. | 73/150 A |
| 4,606,225 | 8/1986 | Thomason et al. . | |
| 5,127,260 | 7/1992 | Robertson | 73/37 |
| 5,361,639 | 11/1994 | Thorsen . | |

Primary Examiner—Ronald L. Biegel
Attorney, Agent, or Firm—Joseph W. Malleck

[57] ABSTRACT

An apparatus for testing the adhesion quality of a coating on the interior surface of a hollow cylindrical substrate, and a method for its use, the apparatus comprising an element joined to the coating, the element having a joining face at one end, a neck at the other end for pulling in a direction perpendicular to the joining face, and a channel through the element aligned with the direction of pulling; a non-adhering plug present in the channel of the element effective to be maintained in contact with the coated surface while extending through and out of said element; a die cut adhesive disc gluing the face of the element to the coated surface as a result of pressure and heat, said disc having a die cut circumference and inner opening commensurate with the size of the plug extending therethrough; a piston and piston housing assembly in which the piston housing is slidable on the piston in response to pressure and has an extension circumferentially overlapping the neck of the element to place a substantially pure tension force on the element when the housing slides away from the coating, the piston remaining engaged with the plug which in turn stays in solid contact with the coated substrate; and a hydraulic pressure supply effective to exert a force between the piston and piston housing to pull the cylinder housing and the element away from the coated surface.

13 Claims, 3 Drawing Sheets

MEASURING ADHESION OF CYLINDER BORE COATINGS

BACKGROUND OF THE INVENTION

1. Technical Field

This invention relates to the technology of accurately determining the degree to which a coating adheres to an inaccessible internal bore surface and more particularly to increasing the range and accuracy of test results when measuring the adhesion of thermally sprayed particulate coatings on metallic cylinder bore surfaces of an engine block.

2. Discussion of the Prior Art

Prior art devices tend to either (i) test the strength of small coated substrate specimens and not the actual assembly itself, thereby sometimes rendering false readings, (ii) require the destruction or dismantling of the substrate for access to a coated surface that is internal, (iii) produce a scatter of test results that fail to accurately depict the true adhesion strength of a curvilinear coated surface because of the presence of unwanted bending moments from the test device or the non-uniform adhesion of the pulling element of the test device to the coating, or (iv) not work with coatings that have ultra high adhesive strengths, such as thermally sprayed metallic particulate coatings, sprayed onto substrates such as aluminum.

SUMMARY OF THE INVENTION

It is an object of the this invention to overcome the deficiencies of the prior art indicated above while providing a test apparatus which fits into a cylinder bore of an internal combustion engine block and employs a method that is easier and faster to test coatings having high adhesive strengths in excess of 4000 psi.

In a first aspect, the invention is a method of testing the adhesion of a coating to an internal cylindrical bore surface, comprising the steps of: (a) gluing an element to be pulled normal to a defined patch of the coating, the element carrying an annular neck surface and a non-glued plug extending centrally through and out of the element for engagement with the coated surface; (b) placing a pulling head about the element, the head having a relatively stationary piston engaged with the plug which in turn is engaged with the coated surface, the head having a slidable piston housing circumferentially overlapping the neck to place substantially pure tension on the element when sliding on the piston; (c) applying a hydraulic force between the piston housing and the piston to pull the housing and element away from the substrate at a controlled rate; and (d) monitoring the hydraulic force to render an indication of the force used to destructively pull the coating attached to the element away from the substrate.

The gluing may be effected by forming such element with (i) a joining face at one end; (ii) a neck at the other end for pulling in a direction perpendicular to the joining face, and (iii) a channel through the element aligned with the direction of pulling. The element, a non-adhering plug, an adhesion disc and the coated substrate are assembled together by pressing the face of the element against the coated substrate with the disc therebetween, the plug being present in the element channel to extend through the disc to engage the coated surface. The assembly is then subjected to heat to set the adhesive disc thereby cementing the element to the coating with the element axis perpendicular to the interior surface carrying such coating.

The invention, in a second aspect, is an apparatus for testing the adhesion quality of a coating on the interior surface of a hollow cylindrical substrate. The apparatus comprises an element joined to the coating, the element having a joining face at one end, a neck at the other end for pulling in a direction perpendicular to the joining face, and a channel through the element aligned with the direction of pulling; a non-adhering plug present in the channel of the element effective to be maintained in contact with the coated surface while extending through and out of said element; a die cut adhesive disc gluing the face of the element to the coated surface as a result of pressure and heat, said disc having a die cut circumference and inner opening commensurate with the size of the plug extending therethrough; a piston and piston housing assembly in which the piston housing is slidable on the piston in response to pressure and has an extension circumferentially overlapping the neck of the element to place a substantially pure tension force on the element when the housing slides away from the coating, the piston remaining engaged with the plug which in turn stays in solid contact with the coated substrate; and a hydraulic pressure supply effective to exert a force between the piston and piston housing to pull the cylinder housing and the element away from the coated surface.

Preferably the overlap contact area or diameter of the slidable housing relative to the diameter of the element face is in a ratio of about 1.6 to 1.2:1 In addition, the diameter of the hydraulic force receiving surface of the piston is generally about 1.5–2.0 times greater than the contact diameter area of the overlap. The slidable cylinder housing rides on an axial arm of the piston to maintain perfect normality to the coated surface and thereby assure that the pulling head will be substantially devoid of bending forces on the element. The assembly has a dimension extending diametrically across the bore which is no greater than 2.0 to 3.0 times the length of the element.

DETAILED DESCRIPTION AND BEST MODE

The accuracy of most prior art adhesion testers suffer from essentially two problems, either the glued element to be pulled, (i.e., dolly) is threaded to the pulling head allowing for the introduction of bending moments instead of pure tension, or (ii) cannot fit within an internal coated bore (e.g., 3–8 inches in diameter) and thereby is unable to accurately test coatings having adhesion forces of 4000 psi or greater.

Figure 1:
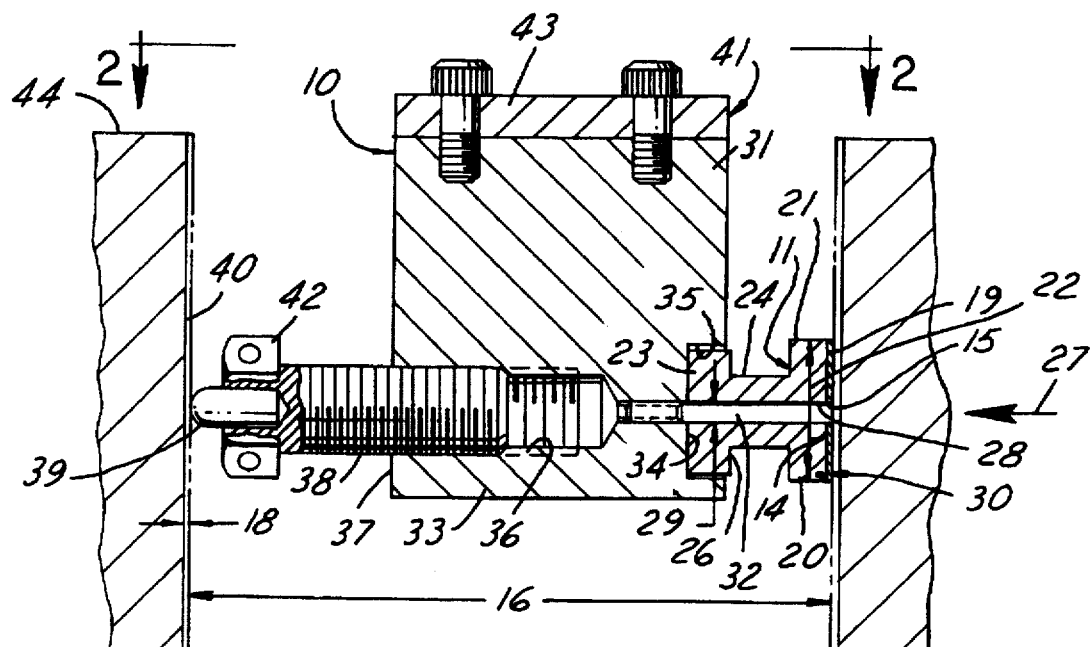
FIG. 1 is an central sectional elevational view of a coated cylinder bore of an internal combustion engine, showing a test element glued to a portion of the coating by use of a pressure applying fixture.
Figure 2:
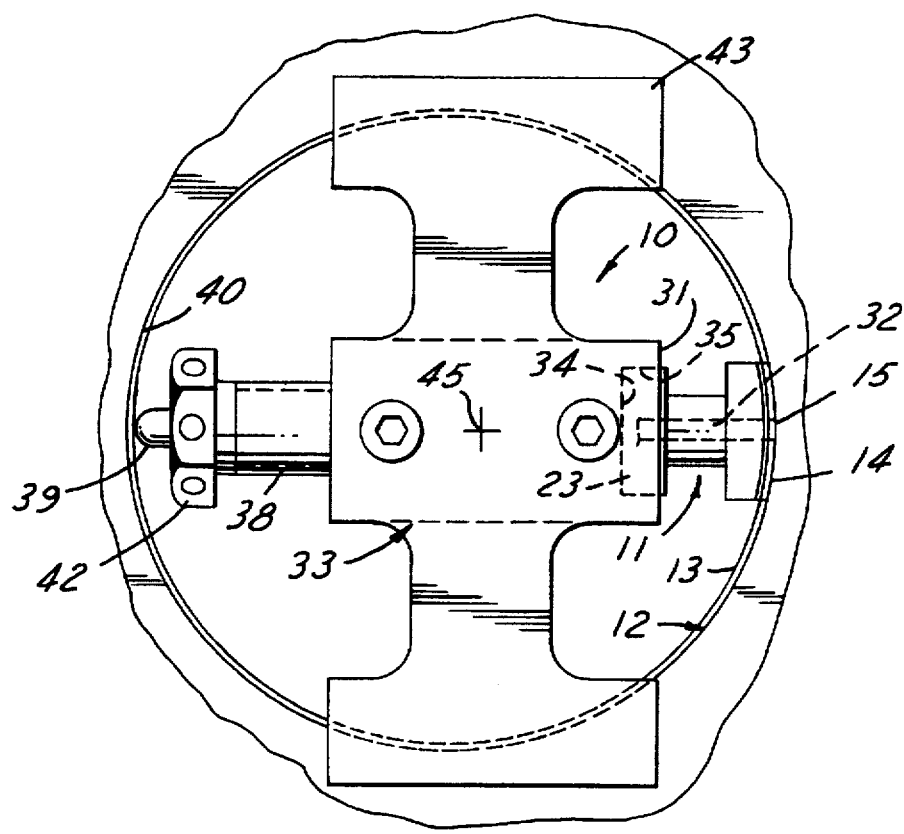
FIG. 2 is a plan view taken along line 2—2 of the apparatus in FIG. 1.

As shown in FIGS. 1–2, the method of this invention first uses a pressure fixture 10 to accurately adhere the pulling element 11 to the surface of the internal coating 13 by use of a thermal-set thin die-cut adhesion disc 14 that possesses a central cut-out opening 15 causing the disc to be washerlike in shape. The coated surface is on a cylinder bore wall 12 of an internal combustion engine block, such bore having an internal diameter 16 (typically 3–8 inches). The coating 13 desirably has a chemistry created by the thermal spraying of steel or other hard metal particles along with lubricious particles to provide a composite coating. Thermal spraying may be by wire arc or powder plasma techniques which deposit droplets or semi melted particles at high velocities and high temperatures; the agglomerated particles in the coating achieve a metallurgical as well as physical or mechanical bond with the substrate (bore wall) that is intended to be 4000 psi or greater. Such coating 13 usually has a thickness 18 in the range of 0.006–0.020 inch.

The pulling element 11 is advantageously comprised of a strong material such as stainless steel or chrome alloy steel (air hardening). The element has a joining face 19 at one end 20 which has a curvilinear shape designed to be complimentary to the curvature of the substrate surface 12. The main body 21 of the element is a cylinder having a diameter 22 of about 0.75 inch; at the other end 23 of the element, is provided a neck 24 which is defined by grooving the exterior of the body 21 to define a radially flat annular surface 26 facing in a direction toward the coated surface 12 which will be receptive to a pulling force in a direction perpendicular to the surface 12 and joining face 19. The element also possesses a central channel 28 extending therethrough which is aligned with the intended direction of pulling 27 and has an internal diameter 29 of about 0.15 inch The adhesive disc 14 has a thickness 30 of about 0.040 inch, and possesses a chemistry preferably consisting essentially of cyanoacrylate. This adhesive is used because it thermosets at a temperature of about 25° C. with a curing time of 15–30 minutes requiring a pressure of 2000–3000 psi during such curing time. Any adhesive can be used that will achieve a-strong uniform bond across the face of the element and that desirably sets up within a short period of time under reasonable pressure and temperature. It is important that the disc 14 have a central opening 15 with a diameter that is commensurate with the diameter of central channel 28 (i.e. about 0.15 inch); the opening allows use of a non-adhering plug 32 extending there-through. The plug may consist of teflon or other equivalent material that is not readily adhered to the die-cut disc 14 when subjected to heat. The plug is designed to occupy the channel 28 of the pulling element 11 without imposition of pressure.

The pressure fixture 10 is utilized to apply sufficient pressure in an accurate direction perpendicular to the element face 19 and disc 14.

The pressure fixture 10 is comprised of a turnbuckle body 33 having a pressure applying surface 34 (here formed in a recess 35 at one side 31 of the body). The body 33 has a threaded socket 36 at the other side 37. A stud 38 is threadably received within the socket 36 and carries a nose 39 effective to create a point contact with the coating on side 40 of the cylindrical surface opposite to that engaged by the pulling element and adhesive disc. The stud is turned by wrenching the surfaces 42 to cause the turnbuckle body 33 to advance away from the stud 38 (engaged with wall 12 through nose 39) and thereby apply pressure to the end 23 of the pulling element containing teflon plug 32. This creates an accurate force normal to the coated surface that insures uniform pressure across the adhesive disc to create an accurate and homogeneous gluing therebetween. The accuracy of the pressure force applied by the fixture 10 is insured by a rigid extension 41 of body 33 that carries a flat squaring wall 43 that does not enter the cylinder bore but fits flush across the machined entrance face 44 and is thereby aligned perpendicular to the axis 45 of the cylinder bore and automatically perpendicular to surface 12 of such coated bore. Once the element 11 is glued in place, fixture 10 is removed without disturbing the element 11 by oppositely wrenching stud 38 to release it from side 40 and thus allow clearing of the element 11 and raising of the fixture 10.

Figure 3:
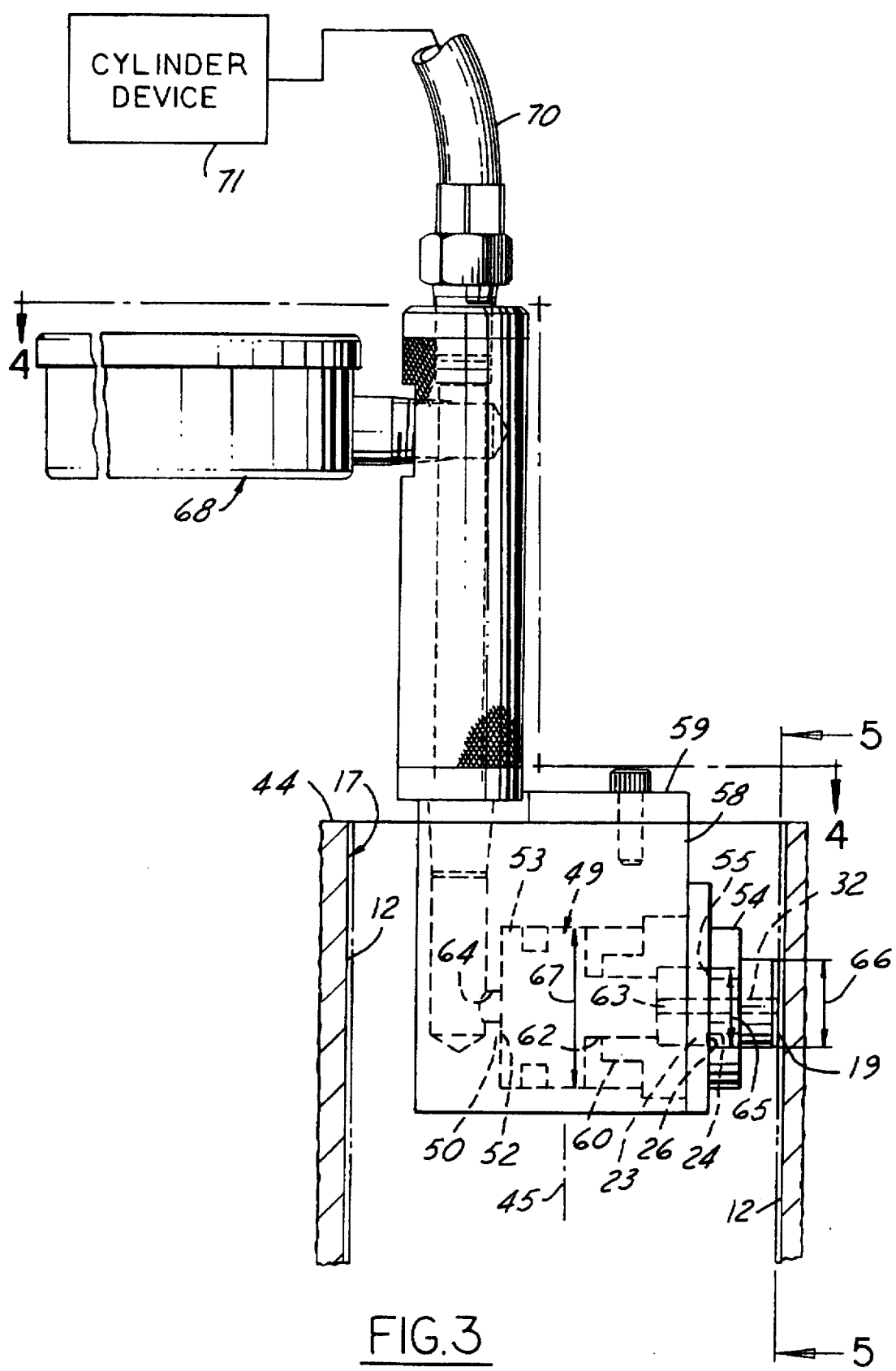
FIG. 3 is an elevational view of the same coated cylinder bore and glued element, but showing a pulling head inserted into the bore and about the element.
Figure 4:
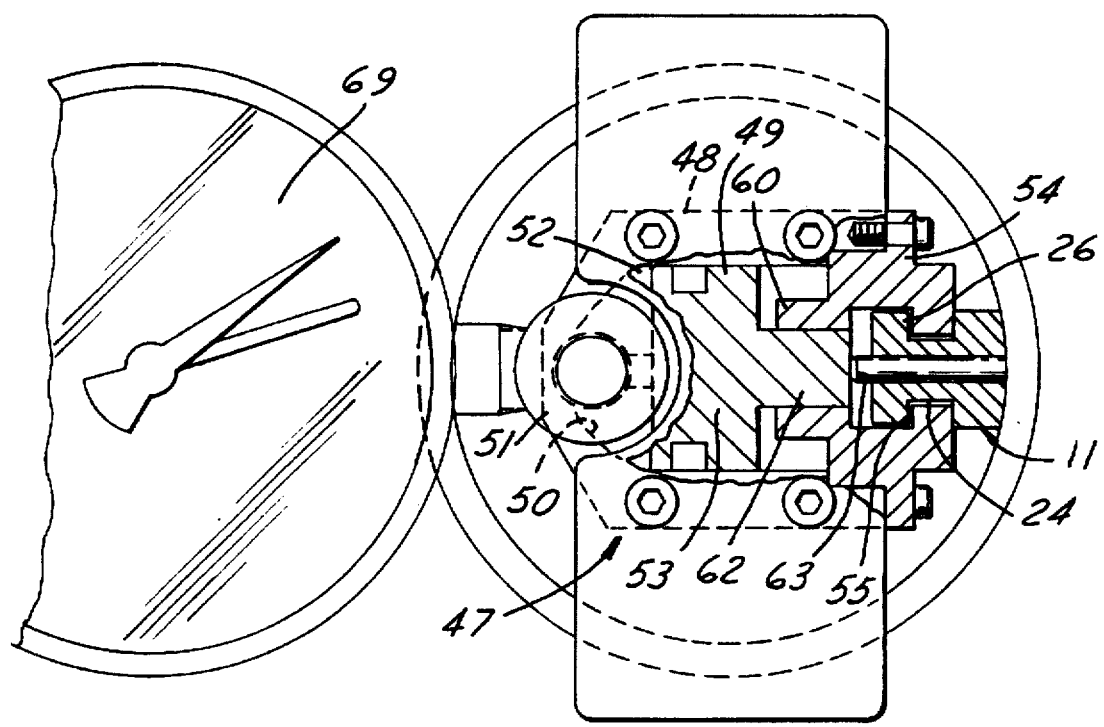
FIG. 4 is a view taken along line 4—4 of the apparatus in FIG. 3 and showing a portion of the pulling head in section.
Figure 5:
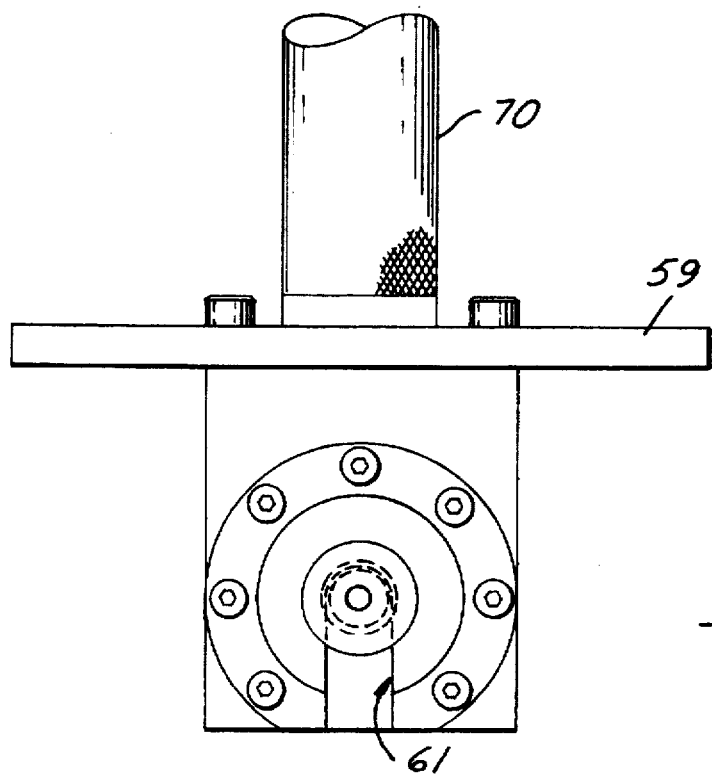
FIG. 5 is a view taken along line 5—5 of FIG. 3.

As shown in FIGS. 3–5, the fixture 10 is now replaced with a piston and cylinder pulling head 47 comprised of a piston housing 48 sealingly slidable on a piston 49. The head 47 is dropped onto the element 11 by virtue a stepped slot 61 that permits the piston housing to slip snugly over the neck 24 and end 23 of the element. The housing is closed at one end 50 (except for supply of pressure through end 50 that communicates hydraulic pressure to an actuating chamber 52 defined between end 50 and the piston head 53). The other end of the housing carries a slotted extension 54 that fits onto and around the neck 24 of element 11 and which has a substantially annular surface 55 that mates with the annular surface 26 to permit application of a pulling force to element 11 that is essentially perpendicular to face 19 of the element and devoid of bending moments. Such perpendicularity is assured in several respects: (i) the housing has a rigid extension 58 that carries a flat squaring wall 59 that does not enter the cylinder bore 17 but fits flush against the machined entrance face 44 of the bore and is thus automatically squared or made perpendicular to the axis 45 of the bore and perpendicular to surface 12; (ii) the housing extension 54 has a sleeve 60 that sealingly slides on a reduced portion 62 of the piston 49 to gain additional squareness to the axis 45 and surface 12; and (iii) the connection between the element 11 and piston housing 48 is only through contact of flat mating surfaces (26, 55) that are aligned perpendicular to the axis 45 and surface 12 before the pulling effort is started.

The extension 54 overlaps the neck 24 of the element to place substantially a pure tension pulling force on the element 11 when sliding away from the coating. The piston remains stationary during the pulling action by contacting end 63 of plug 32 that is engaged with the coated surface. The source of hydraulic pressure for the actuating chamber 52 is a portable piston and cylinder device 71 stationed outside of the coated bore and employs a mechanical advantage to permit manual build-up of pressure to about 2500 psi in a flexible pressure line 70 connecting to the port 64 of the slidable housing that is in communication with the actuating chamber 52.

The mean diameter 65 of overlap contact is slightly less than the diameter 66 of the element face 19, while the diameter 67 of piston 49 is about twice the diameter of the element face 19 giving an advantage of about a 2:1. A pressure gauge 68, with a dial 69, is interposed in the line 70 to permit monitoring of the supplied hydraulic force and thereby allow a rendering (by mathematical conversion) of an indication of the force needed to pull away the area of the coating glued to the element face 19. It is desirable to conduct only about three tests to provide assurance of a mean average adhering value, assuming the same element face diameter is employed each time. The reduced number of tests that is now required is due to the reduced scatter and increased reliability of the results of this apparatus and method.

While particular embodiments of the invention have been illustrated and described, it will be obvious to those skilled in the art that various changes and modifications may be made without departing from the invention, and it is intended to cover in the appended claims all such modifications and equivalents as fall within the true spirit and scope of this invention.

I claim:

1. A method of testing the adhesion of a coating to an internal cylindrical bore surface, comprising:
   (a) gluing an element to be pulled normal to a defined patch of the coating, said element carrying an annular neck surface parallel to said coating patch and a non-glued plug extending centrally through and out of the element for engagement with the coated surface;
   (b) placing a pulling head about the element by movement thereonto in a linear direction parallel to said patch of coating, said head having a relatively stationary piston engaged with said plug and a slidable piston housing circumferentially overlapping said neck surface to place substantially pure tension on said element when sliding on said piston;
   (c) applying a hydraulic force between the piston housing and piston to pull the piston housing and element away from the coated surface at a controlled rate; and
   (d) monitoring said hydraulic force to render an indication of the force used to destructively pull the coating attached to the element away from the coated surface.

2. The method as in claim 1, in which gluing is effected by forming the element to be joined to the coating with (i) a joining face at one end, (ii) a flat neck surface at the other end for pulling in a direction perpendicular to the joining face, and (iii) a channel through the element aligned with the direction of pulling, the element, the non-adhering plug, adhesive disc and coating being assembled by pressing the face of the element against the coating with said disc therebetween and with said plug present in the channel to extend through the disc to engage the coated surface, said pressing being effected by reacting a pressing force against the opposite side of said bore from the coating patch being tested, the assembly being heated to cement the element to the coating while pressure is applied to the element to cooperate with said required thermo-setting.

3. The method as in claim 1, in which the coating that is to be tested is one in which thermally sprayed metallic particles are coated onto an aluminum cylinder bore, said particles containing steel and solid lubricants.

4. A method of testing the adhesion of a coating to an internal cylindrical bore surface, comprising:
   (a) gluing an element to be pulled normal to a defined patch of the coating, said element being glued to the coating by use of a die-cut thermosetting adhesive disc having a central opening through which said plug extends;
   (b) placing a pulling head about the element by movement thereonto in a linear direction parallel to said patch of coating, said head having a relatively stationary piston engaged with said plug and a slidable piston housing circumferentially overlapping said neck surface to place substantially pure tension on said element when sliding on said piston;
   (c) applying a hydraulic force between the piston housing and piston to pull the piston housing and element away from the coated surface at a controlled rate; and
   (d) monitoring said hydraulic force to render an indication of the force used to destructively pull the coating attached to the element away from the coated surface.

5. The method as in claim 4, in which said disc has a thickness of about 0.040 inch and is comprised of cyanoacrylate settable at a temperature of about 25° C. accompanied by a pressure of about 2000–3000 psi.

6. A method of testing the adhesion of a coating to an internal cylindrical bore surface, comprising:
   (a) gluing an element to be pulled normal to a defined patch the coating, said element carrying an annular neck surface parallel to said coating patch and a non-glued plug extending centrally through and out of the element for engagement with the coated surface, the neck of said element being defined by an annular groove lying in a plane parallel to the joining face of the element to present a pulling surface away from the coating;
   (b) placing a pulling head about the element by movement thereonto in a linear direction parallel to said patch of coating, said head having a relatively stationary piston engaged with said plug and a slidable piston housing circumferentially overlapping said neck surface to place substantially pure tension on said element when sliding on said piston, the housing having an extension with a annular surface mateable with and parallel to said element pulling surface which overlaps said neck to allow for imparting pure tension pulling action on said element;
   (c) applying a hydraulic force between the piston housing piston to pull the piston housing and element away from the coated surface at a controlled rate; and
   (d) monitoring said hydraulic force to render an indication the force used to destructively pull the coating attached to the element away from the coated surface.

7. A method of testing the adhesion of a coating to an internal cylindrical bore surface, comprising:
   (a) gluing an element to be pulled normal to a defined patch of the coating, said element carrying an annular neck surface parallel to said coating patch and a non-glued plug extending centrally through out of the element for engagement with the coated surface;
   (b) placing a pulling head about the element by movement thereonto in a linear direction parallel to said patch of coating, said head having a relatively stationary piston engaged with said plug and a slidable piston housing circumferentially overlapping said neck surface to place substantially pure tension on said element when sliding on said piston, the piston housing being aligned perpendicular to the axis of the bore and perpendicular to the coating, the piston housing having an extension extending out of the bore to be squared with the entrance to the bore and thereby assuring said perpendicularity;
   (c) applying a hydraulic force between the piston housing and piston to pull the piston housing and element away from the coated surface at a controlled rate; and
   (d) monitoring said hydraulic force to render an indication of the force used to destructively pull the coating attached to the element away from the coated surface.

8. A method of measuring the adhesion quality of a coating on the interior surface of a hollow cylindrical substrate, the substrate having an entrance lying in a plane that is at a predetermined angle to the axis of such interior surface, comprising:
   (a) forming an element to be joined to the coating, said element having (i) a joining face at one end, (ii) a neck at the other end for pulling in a direction perpendicular to the joining face, and (iii) a channel through the element aligned with the direction of pulling;
   (b) assembling said element, a non-adhering plug, and an adhesive disc and the coated substrate by pressing the face of said element against said coated substrate with said disc therebetween while imposing a pressure that is suitable for achieving proper adherence, said plug being present in the channel to extend through said disc to engage the coated substrate;

(c) subjecting said assembly to heat to set the adhesive disc in Conjunction with the pressure applied, thereby cementing the element to the coating with its axis perpendicular to the interior surface carrying such coating;

(d) inserting a piston and cylinder pulling head into said hollow substrate to reach said assembly, said head having a pressure reactive cylinder housing aligned to slide along the axis of the cemented element and in a direction away from the coating, said housing circumferentially overlapping the neck of said element to place a substantially pure tension force on said element when sliding away from the coating, said head also comprising a piston within the housing and upon which the housing slides, said piston normally reacting in response to pressure to remain engaged and stationary with the plug that is in solid contact with the substrate;

(e) applying a hydraulic force between the housing and piston to pull the housing and element away from the coated substrate at a controlled rate; and (f) monitoring the hydraulic force to render an indication of the force used to destructively pull the coating attached to the disc away from the substrate.

9. The method as in claim 8, in which the ratio of the diameter of the element face to the diameter of the channel is in the range of 2.1.

10. The method as in claim 8, in which the annular overlap contact area between the element and piston housing providing a mean pulling diameter, the mean pulling diameter being equal to slightly less than the diameter of the face adhered to the coating.

11. The method as in claim 8, in which the ratio of the diameter of the piston to the diameter of the face adhered to the coating is about 2:1.

12. The method as in claim 8, in which perpendicularity and pure tension forces are assured during pulling by (i) aligning the element during thermosetting using of a fixture that has an extension outside the coated bore fitting flush and square with the entrance and axis of the bore and (ii) aligning the piston housing during pulling by use of a housing extension outside the coated bore which is flush and square with the entrance and axis of the bore.

13. An apparatus assembly for testing the adhesion quality of a coating on the interior surface of a hollow cylindrical substrate, comprising:

(a) an element to be pulled that is glued to a patch of the interiorly coated substrate, the element having an annular neck surface and a non-glued plug extending centrally through the element to avoid gluing of the element at its face center;

(b) a piston and cylinder device having a head disposed within the coated bore with a related piston engaging the plug and a slideable piston housing circumferentially overlapping the element neck to place substantially pure tension on the element when actuated to slide on the piston;

(c) means for supplying hydraulic pressure between said piston and slideable housing, said means having a pump located outside of said bore and effective to communicate with said pulling device by a flexible line; and (d) means for monitoring the hydraulic force to render an indication of the force used to destructively pull the coating attached to the element away from the substrate.

* * * * *